US011607136B2

(12) United States Patent
Nelson et al.

(10) Patent No.: US 11,607,136 B2
(45) Date of Patent: Mar. 21, 2023

(54) SYSTEM AND METHOD FOR CONFORMAL VISION

(71) Applicant: ChemImage Corporation, Pittsburgh, PA (US)

(72) Inventors: Matthew Nelson, Harrison City, PA (US); Thomas Voigt, Export, PA (US); Maxxwell Chatsko, Pittsburgh, PA (US); Patrick Treado, Pittsburgh, PA (US); Rebecca Schuler, Pittsburgh, PA (US); Shona Stewart, Pittsburgh, PA (US); James McGlone, Newtown Square, PA (US); Oksana Klueva, Pittsburgh, PA (US); Nathaniel Gomer, Pittsburgh, PA (US)

(73) Assignee: CHEMIMAGE CORPORATION, Pittsburgh, PA (US)

( * ) Notice: Subject to any disclaimer, the term of this patent is extended or adjusted under 35 U.S.C. 154(b) by 405 days.

(21) Appl. No.: 16/650,310

(22) PCT Filed: Jul. 24, 2018

(86) PCT No.: PCT/US2018/043495
§ 371 (c)(1),
(2) Date: Mar. 24, 2020

(87) PCT Pub. No.: WO2019/023236
PCT Pub. Date: Jan. 31, 2019

(65) Prior Publication Data
US 2020/0229703 A1    Jul. 23, 2020

Related U.S. Application Data

(60) Provisional application No. 62/536,094, filed on Jul. 24, 2017.

(51) Int. Cl.
*A61B 5/00*     (2006.01)
*A61B 5/0205*   (2006.01)
(Continued)

(52) U.S. Cl.
CPC .......... *A61B 5/0079* (2013.01); *A61B 5/0205* (2013.01); *G01J 3/0224* (2013.01);
(Continued)

(58) Field of Classification Search
CPC ................ A61B 5/0079; A61B 5/0205; A61B 5/0261; A61B 5/08; A61B 5/1032;
(Continued)

(56) References Cited

U.S. PATENT DOCUMENTS

2008/0194928 A1   8/2008  Bandic et al.
2013/0321813 A1   12/2013 Treado et al.
(Continued)

FOREIGN PATENT DOCUMENTS

JP   2010-515489 A   7/2008
JP   2011-509154 A   7/2009

OTHER PUBLICATIONS

Nelson et al., "Performance Evaluation and Modeling of a Conformal Filter (CF) Based Real-Time Standoff Hazardous Material Detection Sensor," Proceedings of SPIE, May 3, 2017; vol. 10210, pp. 102100L 1-10.

*Primary Examiner* — Md M Rahman
(74) *Attorney, Agent, or Firm* — DLA Piper LLP (US)

(57) ABSTRACT

Conformal vision with enhanced image processing of the outputted image is incorporated into novel applications. The conformal vision provides enhanced contrast by the combined inclusion of tunable filters and processing of the images that are generated by the detector. Furthermore, novel uses and applications of the conformal vision enable users to make determinations related to their health and
(Continued)

wellness utilizing information provided by the conformal vision.

24 Claims, 14 Drawing Sheets

(51) Int. Cl.
  *G01J 3/02* (2006.01)
  *G01J 3/26* (2006.01)
  *G01J 3/447* (2006.01)
  *G01N 21/31* (2006.01)
  *A61B 5/026* (2006.01)
  *A61B 5/08* (2006.01)
  *A61B 5/103* (2006.01)
  *A61B 5/1455* (2006.01)
  *A61B 5/16* (2006.01)

(52) U.S. Cl.
  CPC ............ *G01J 3/0227* (2013.01); *G01J 3/0237* (2013.01); *G01J 3/0264* (2013.01); *G01J 3/26* (2013.01); *G01J 3/447* (2013.01); *G01N 21/31* (2013.01); *A61B 5/0261* (2013.01); *A61B 5/08* (2013.01); *A61B 5/1032* (2013.01); *A61B 5/14551* (2013.01); *A61B 5/165* (2013.01); *A61B 5/441* (2013.01); *A61B 5/4878* (2013.01); *A61B 2562/0233* (2013.01)

(58) Field of Classification Search
  CPC ..... A61B 5/14551; A61B 5/165; A61B 5/441; A61B 5/4878; A61B 2562/0233; G01J 3/0224; G01J 3/0227; G01J 3/0237; G01J 3/0264; G01J 3/26; G01J 3/447; G01J 3/0272; G01J 2003/1213; G01J 3/36; G01J 3/32; G01N 21/31; G01N 21/25; G02F 1/13306; G02F 1/13471; G02F 1/213; G02F 2201/38; G02F 2203/055; G02F 1/0136; G02F 2202/40
  USPC ......................................................... 356/310
  See application file for complete search history.

(56) References Cited

U.S. PATENT DOCUMENTS

2014/0198315 A1    7/2014   Priore et al.
2015/0133751 A1    5/2015   Stewart et al.

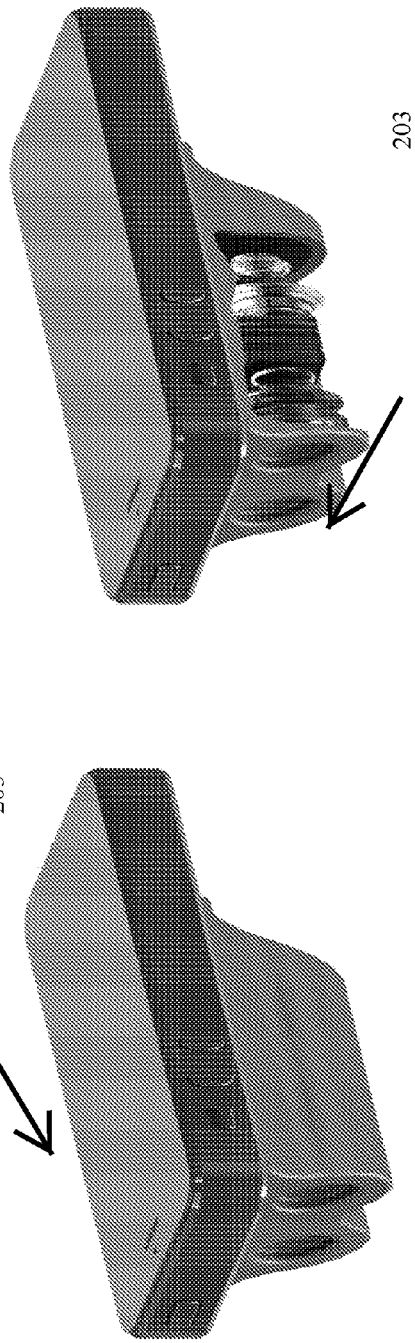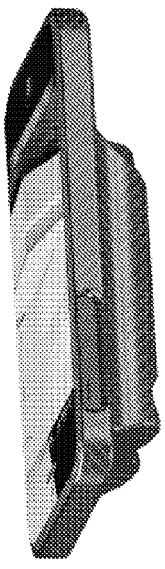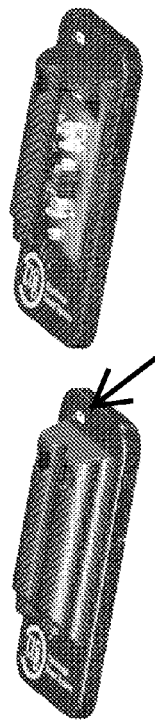
FIG. 6A  FIG. 6B  FIG. 6C  FIG. 6D  FIG. 6E
Conformal Vision integrated with iPhone (cutaway view at right)

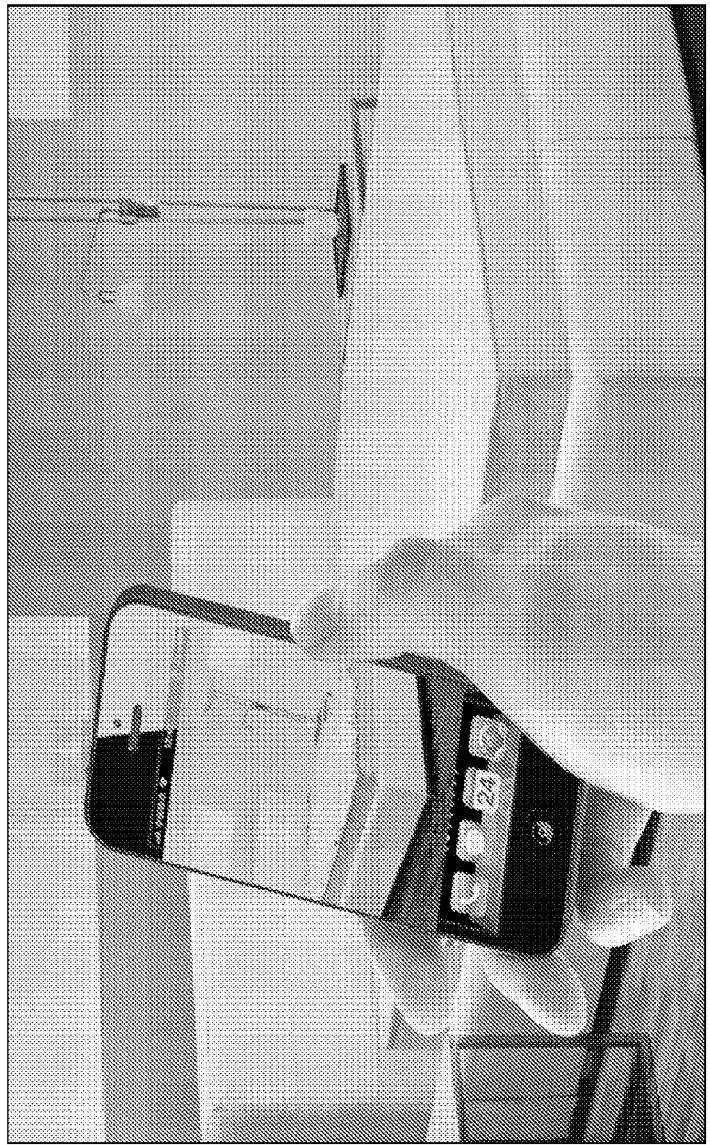
FIG. 7 CV Detection of Bed Bugs

SYSTEM AND METHOD FOR CONFORMAL VISION

CLAIM OF PRIORITY

This application claims the benefit of priority to U.S. Provisional Application No. 62/536,094 titled "SYSTEM AND METHOD FOR CONFORMAL VISION," filed Jul. 24, 2017, which is incorporated herein by reference in its entirety.

BACKGROUND

Spectroscopic imaging combines digital imaging and molecular spectroscopy techniques, which can include Raman scattering, fluorescence, photoluminescence, ultraviolet, visible and infrared absorption spectroscopies. When applied to the chemical analysis of materials, spectroscopic imaging is commonly referred to as chemical imaging. Instruments for performing spectroscopic (i.e. chemical) imaging typically comprise an illumination source, image gathering optics, focal plane array imaging detectors and imaging spectrometers.

In general, the size of a sample determines the choice of image gathering optic. For example, a microscope is typically employed for the analysis of sub-micron to millimeter spatial dimension samples. For larger objects, in the range of millimeter to meter dimensions, macro lens optics are appropriate. For samples located within relatively inaccessible environments, flexible fiberscope or rigid borescopes can be employed. For very large scale objects, such as planetary objects, telescopes are appropriate image gathering optics.

For detection of images formed by the various optical systems, two-dimensional, imaging focal plane array ("FPA") detectors are typically employed. The choice of FPA detector is governed by the spectroscopic technique employed to characterize the sample of interest. For example, silicon (Si) charge-coupled device ("CCD") detectors or complementary metal-oxide semiconductor ("CMOS") detectors are typically employed with visible wavelength fluorescence and Raman spectroscopic imaging systems, while indium gallium arsenide ("InGaAs") FPA detectors are typically employed with near-infrared spectroscopic imaging systems.

Spectroscopic imaging of a sample is commonly implemented by one of two methods. First, point-source illumination can be used on a sample to measure the spectra at each point of the illuminated area. Second, spectra can be collected over the entire area encompassing a sample simultaneously using an electronically tunable optical imaging filter such as an acousto-optic tunable filter (AOTF), a multi-conjugate tunable filter (MCF), or a liquid crystal tunable filter (LCTF). Here, the organic material in such optical filters is actively aligned by applied voltages to produce the desired bandpass and transmission function. The spectra obtained for each pixel of an image forms a complex data set referred to as a hyperspectral image. Hyperspectral images may contain the intensity values at numerous wavelengths or the wavelength dependence of each pixel element in the image. Multivariate routines, such as chemometric techniques, may be used to convert spectra to classifications.

Spectroscopic devices operate over a range of wavelengths depending on the operation ranges of the detectors or tunable filters possible. This enables analysis in the ultraviolet (UV), visible (VIS), near infrared (NIR), short-wave infrared (SWIR), mid infrared (Milt), long wave infrared (LWIR) wavelengths, and to some overlapping ranges. These correspond to wavelengths of approximately 180-380 nm (UV), 380-700 nm (VIS), 700-2500 nm (NIR), 850-1800 nm (SWIR), 650-1100 nm (MWIR), 400-1100 (VIS-NIR) and 1200-2450 nm (LWIR).

A LCTF uses birefringent retarders to distribute the light energy of an input light signal over a range of polarization states. The polarization state of light emerging at the output of the LCTF is caused to vary as a function of wavelength due to differential retardation of orthogonal components of the light, contributed by the birefringent retarders. The LCTF discriminates for wavelength-specific polarization using a polarizing filter at the output. The polarizing filter passes the light components in the output that are rotationally aligned to the polarizing filter. The LCTF is tuned by adjusting the birefringence of the retarders so that a specific discrimination wavelength emerges in a plane polarized state, aligned to the output polarizing filter. Other wavelengths that emerge in other polarization states and/or alignments are attenuated.

A highly discriminating spectral filter is possible using a sequence of several birefringent retarders. The thicknesses, birefringences, and relative rotation angles of the retarders are chosen to correspond to the discrimination wavelength. More specifically, the input light signal to the filter becomes separated into orthogonal vector components, parallel to the respective ordinary and extraordinary axes of each birefringent retarder when encountered along the light transmission path through the filter. These separated vector components are differentially retarded due to the birefringence; such differential retardation also amounts to a change in their polarization state. For a plane polarized component at the input to the filter, having a specific rotational alignment at the input to the filter and at specific discrimination wavelengths, the light components that have been divided and subdivided all emerge from the filter in the same polarization state and alignment, namely plane polarized and in alignment with the selection polarizer (i.e., the polarizing filter) at the output.

A filter as described is sometimes termed an interference filter because the components that have been divided and subdivided from the input and interfere positively at the output selection polarizer are the components that are passed. Such filters also are sometimes described with respect to a rotational twist in the plane polarization alignment of the discriminated component between the input and the selection polarizer at the output.

There are several known configurations of spectral filters comprising birefringent retarders, such as the Lyot, Solc and Evans types. Such filters can be constructed with fixed (non-tunable) birefringent crystals for the retarders. A filter with retarders that are tuned in unison permits adjustment of the bandpass wavelength. Tunable retarders can comprise liquid crystals or composite retarder elements each comprising a fixed crystal and an optically aligned liquid crystal.

The thicknesses, birefringences, and rotation angles of the retarders are coordinated such that each retarder contributes part of the necessary change in polarization state to alter the polarization state of the passband wavelength from an input reference angle to an output reference angle. The input reference angle may be, for example, 45° to the ordinary and extraordinary axes of a first retarder in the filter. The output reference angle is the rotational alignment of the polarizing filter (or "selection polarizer").

A spectral filter may have a comb-shaped transmission characteristic. Increasing or decreasing the birefringence when tuning to select the discrimination wavelength (or passband), stretches or compresses the comb shape of the transmission characteristic along the wavelength coordinate axis.

If the input light is randomly polarized, the portion that is spectrally filtered is limited to the vector components of the input wavelengths that are parallel to one of the two orthogonal polarization components that are present. Only light at the specific wavelength, and at a given reference polarization alignment at the input, can emerge with a polarization angle aligned to the rotational alignment of the selection polarizer at the output. The light energy that is orthogonal to the reference alignment at the input, including light at the passband wavelength, is substantially blocked.

Currently, tunable optical filter technology is limited to single-bandpass, low-throughput operation and passes only one of two orthogonal components of input light. The transmission ratio in the passband is at a maximum for incident light at the input to the LCTF that is aligned to a reference angle of the LCTF. Transmission is at a minimum for incident light energy at the input that is orthogonal to that reference angle. If the input light in the passband is randomly polarized, the best possible transmission ratio in the passband is fifty percent. In addition, multiple discrete bandpass measurements are required for analyte discrimination. The need for multiple measurements translates directly into overall measurement time.

Multivariate Optical Computing (MOC) is an approach which utilizes a compressive sensing device (e.g. an optical computer) to analyze spectroscopic data as it is collected. Other approaches utilize hard coated optical computing filters such as Multivariate Optical Elements (MOEs). MOEs are application-specific optical thin film filters that are used in transmission and reflectance modes. The radiometric response of a MOE-based instrument is proportional to the intended analyte in an associated matrix. While compressive sensing holds potential for decreasing measurement time, the use of MOEs has limitations. For example, MOEs are fixed and lack flexibility for adapting to different analytes.

There exists a need for an adaptable filter that can be used to detect a wide variety of analytes while reducing overall measurement time.

SUMMARY

The present disclosure provides for a system and method for "conformal vision." Conformal vision combines the use of adaptable tunable filters with the flexibility of conforming to a specific, broadband spectral feature (e.g. pattern or shape), arranged in a dual polarization configuration. These filters, referred to herein as "conformal filters," overcome the limitations of the prior art by simultaneously transmitting multiple passbands that improve discrimination performance for analytes (e.g., discriminating between a target analyte and background), by increasing the throughput of a tunable filter, and by increasing the speed of analysis.

The present disclosure provides for a system and method for detecting analytes using a conformal filter in a dual polarization configuration. This "conformal dual polarization module" may be incorporated into a detection device with each conformal filter comprising a tunable filter capable of adapting to a variety of configurations that filter interacted photons conforming to at least one spectral shape associated with an analyte of interest. Each configuration is designed to filter interacted photons conforming to at least one spectral shape associated with an analyte of interest. The conformal filter may be configured to operate in conjunction with a look-up table (LUT), providing flexibility for simultaneously detecting multiple analytes of interest in near real-time or real-time. The LUT may comprise at least one voltage associated with each stage of the tunable filter. Each voltage is configured to cause the tunable filter to conform to a spectral shape associated with the analyte when applied to the associated stage.

A conformal filter as provided for herein is adaptable and may be configured to detect a wide variety of analytes. The conformal filter may also be used to detect analytes using a variety of spectroscopic and chemical imaging modalities.

The present disclosure provides for a method for detecting one or more analytes of interest using a conformal filter. A sample is illuminated to generate at least one plurality of interacted photons that are separated into a first optical component and a second optical component. The first optical component may be passed through a first conformal filter, and the second optical component may be passed through a second conformal filter. Each conformal filter may be tuned independently or in unison and may be configured for the same or for different analytes of interest. At least one test data set is generated that is representative of the sample. A first test data set may be generated corresponding to the first optical component, and a second test data set may be generated corresponding to the second optical component. This test data set(s) may then be analyzed to assess the sample for one or more characteristics of the analyte.

The present disclosure also provides for a system comprising a processor and a non-transitory processor-readable storage medium in operable communication with the processor. The storage medium may contain one or more programming instructions that, when executed, cause the processor to tune at least one of the conformal filters to a configuration to filter interacted photons conforming to a spectral shape associated with an analyte of interest, generate one or more test data sets representative of the sample, and analyze the test data set(s) to assess the sample for at least one characteristic of the analyte.

In one embodiment, a system of the present disclosure may be configured to an ultra compact configuration that is small, light and low-power consuming. The present disclosure contemplates that such a system could be integrated into a cell phone or other portable, wireless device.

Conformal Vision is a form of hyperspectral imaging that uses compressive sensing methods in which all the color bands necessary to discriminate an object of interest from the background are transmitted simultaneously through the liquid crystal conformal filters. As a result, the conformal filters, when operated in conjunction with the dual polarization optical design, collectively acquire object-specific images at the frame rate of a camera, such as a cell phone camera.

In one embodiment, a system for conformal vision includes a conformal filter that includes a tunable filter; a detector that detects interacted photons through the conformal filter; a processor in communication with the detector; and a look-up table (LUT) associated with the conformal filter and which corresponds to an analyte of interest, wherein at the conformal filter tunes to filter interacted photons conforming to a spectral shape associated with the analyte of interest, wherein the processor generates a test data set representative of the sample from the detector, and wherein the processor analyzes the test data set to determine at least one characteristic of the analyte.

In one embodiment, the LUT comprises at least one voltage associated with each stage of each tunable filter.

In one embodiment, each tunable filter is selected from the group consisting of a liquid crystal tunable filter, an acousto tunable filter, a Lyot liquid crystal tunable filter, an Evans Split-Element liquid crystal tunable filter, a Solc liquid crystal tunable filter, a Ferroelectric liquid crystal tunable filter, a Fabry Perot liquid crystal tunable filter, a multi-conjugate filter (MCF) and combinations thereof.

In one embodiment, the system for conformal vision includes a hot mirror.

In one embodiment, the detector is selected from the group consisting of a charged coupled device (CCD) detector, a complementary metal oxide semiconductor (CMOS) detector, an indium gallium arsenide (InGaAs) detector, a platinum silicide (PtSi) detector, a mercury cadmium telluride (HgCdTe) detector, a colloidal quantum dot (CQD) detector, and combinations thereof.

In one embodiment, the system is configured to assess a level of oxygenation in tissue.

In one embodiment, the system is configured to analyze skin for the presence of a rash or an irritant.

In one embodiment, the system is configured for human self-assessment, and wherein the processor is operably coupled to at least one of a television, a mirror, a camera, or a device for projecting an image.

In one embodiment, the human self-assessment is with respect to clothing or physical appearance.

In one embodiment, a method for conformal vision comprises providing a look-up table (LUT) associated with a conformal filter and which corresponds to an analyte of interest, wherein the conformal filter includes a tunable filter, tuning the conformal filters which includes the tunable filter, to filter interacted photons conforming to a spectral shape associated with an analyte of interest, generating, using a processor, a test data set representative of the sample from a detector, and analyzing, using the processor, the test data set to determine at least one characteristic of the analyte.

In one embodiment, the LUT comprises at least one voltage associated with each stage of the tunable filter.

In one embodiment, the at least one tunable filter is selected from the group consisting of a liquid crystal tunable filter, an acousto tunable filter, a Lyot liquid crystal tunable filter, an Evans Split-Element liquid crystal tunable filter, a Solc liquid crystal tunable filter, a Ferroelectric liquid crystal tunable filter, a Fabry Perot liquid crystal tunable filter, a multi-conjugate filter (MCF) and combinations thereof.

In one embodiment, the method further comprises generating a reference data set corresponding to a matrix; applying a chemometric technique to the reference data set, and outputting an enhanced contrast test data set that has enhanced contrast and that is representative of the sample so as to achieve Real-time Contrast Enhancement (RtCE).

In one embodiment, the method further comprises determining whether or not a tolerance level is met by applying at least one Figure of Merit (FOM).

In one embodiment, the FOM is selected from the group consisting of standard error of calibration (SEC), Euclidian Distance, standard error of prediction (SEP), 1-Area Under the Receiver Operator Characteristic Curve (AUROC), optical throughput (% T), and combinations thereof.

In one embodiment, the chemometric technique is selected from the group consisting of correlation analysis, principle component regression, partial least squares, multivariate curve resolution, Mahalanobis distance, Euclidian distance, band target entropy, band target energy minimization, partial least squares discriminant analysis, adaptive subspace detection, and combinations thereof.

In one embodiment, the method also comprises displaying a human self-assessment image based on at least one characteristic of the analyte.

In one embodiment, the human self-assessment image includes information regarding the clothing or physical appearance of the human that is performing the self-assessment.

In one embodiment, displaying the human self-assessment image comprises displaying the human self-assessment image using a television, a mirror, a camera, or a projector.

In one embodiment, a wellness indicating apparatus comprises a conformal filter that includes a tunable filter, wherein the conformal filters tunes to filter interacted photons conforming to a spectral shape associated with an analyte of interest on a sample; a detector; and a processor, wherein the processor: generates a test data set representative of the sample from the detector, analyzes the test data set to determine at least one characteristic of the analyte, correlates the at least one characteristic of the analyte to a determined wellness factor, and communicates the determined wellness factor to a human user.

In one embodiment, the wellness indicating apparatus further comprises a network interface for communicating the determined wellness factor to a human user.

In one embodiment, the wellness indicating apparatus further comprises a display for communicating the determined wellness factor to a human user.

In one embodiment, the wellness indicating apparatus display is selected from the group consisting of a liquid crystal display, an organic light emitting diode display, a projector, an electrophoretic display, a mirror, a cathode ray tube display, a projection display, a heads up display, an augmented reality display and combinations thereof.

In one embodiment, the analyte is related to tissue oxygenation.

In one embodiment, the wellness factor is related to a skin condition, a heart condition, a stress level, a mood, respiration, skin differential blood flow, skin color, edema levels, and combinations thereof.

In one embodiment, a method of assessing wellness comprises providing a conformal filter, wherein the conformal filter includes a tunable filter, providing a detector, providing a processor, wherein the processor is configured to: generate a test data set representative of the sample from the detector, analyze the test data set to determine at least one characteristic of the analyte, correlate the at least one characteristic of the analyte to a determined wellness factor, and communicate the determined wellness factor to a human user.

BRIEF DESCRIPTION OF THE DRAWINGS

The accompanying drawings, which are included to provide further understanding of the disclosure and are incorporated in and constitute a part of this specification illustrate embodiments of the disclosure, and together with the description, serve to explain the principles of the disclosure.

FIG. 1A is illustrative of a conformal filter embodiment. FIG. 1B is illustrative of a conformal filter embodiment comprising a rotatable aperture. FIGS. 1C and 1D are illustrative of a conformal filter embodiment comprising a MCF design. FIG. 1E is illustrative of a conformal filter embodiment utilizing a modified MCF design.

FIG. 6 is illustrative of exemplary housing configurations of a cell phone incorporating conformal vision.

FIG. 7 is representative of an exemplary mode of operation of conformal vision.

DETAILED DESCRIPTION

Figure 1A:
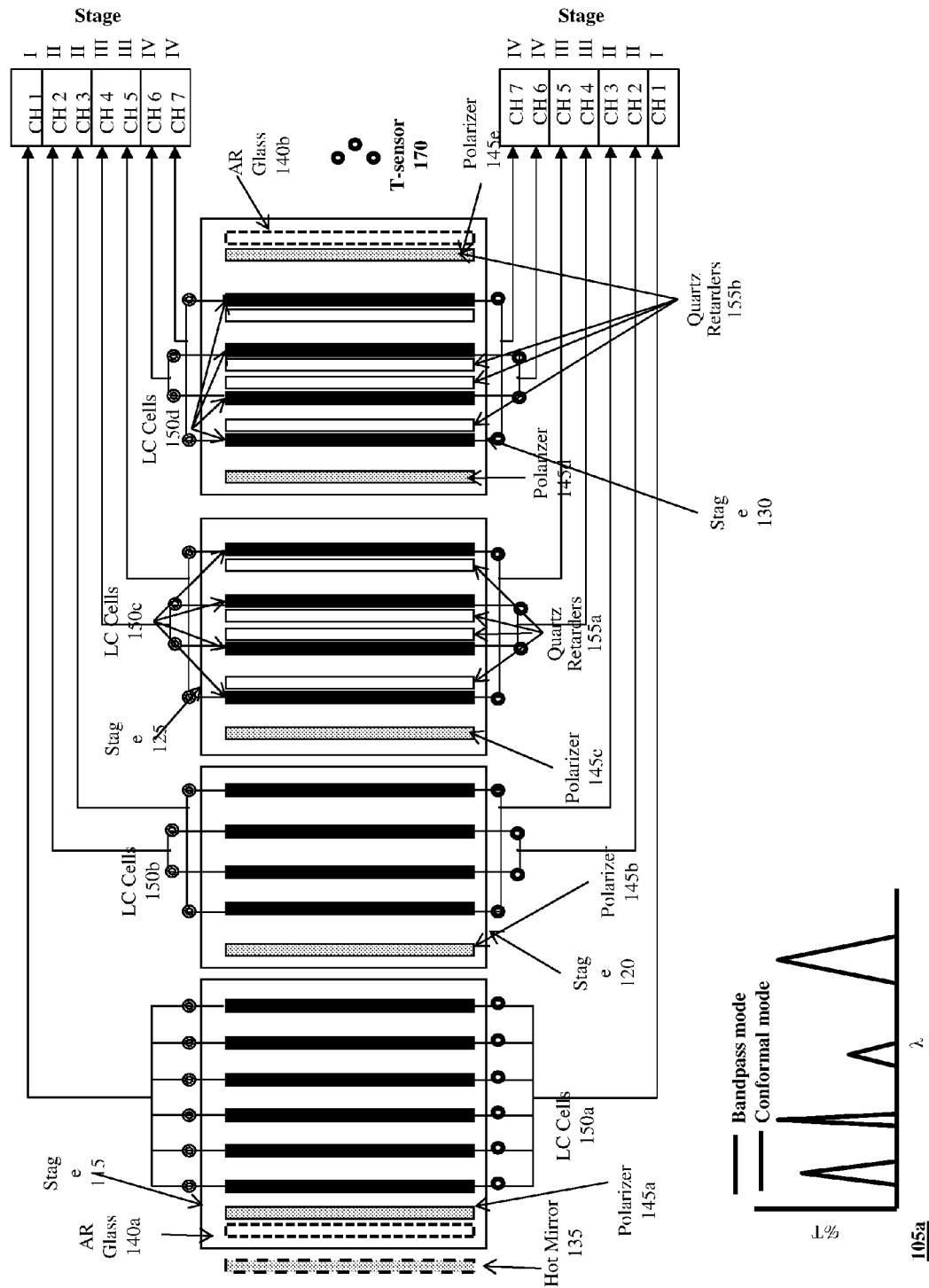
FIGS. 1A-1E are illustrative of exemplary conformal filter embodiments of the present disclosure.

Reference will now be made in detail to the embodiments of the present disclosure, examples of which are illustrated in the accompanying drawings. Wherever possible, the same reference numbers will be used throughout the specification to refer to the same or like parts.

The present disclosure provides for a system and method for detecting one or more analytes of interest using a plurality of conformal filters in a dual polarization configuration.

In one embodiment, the present disclosure provides for a system comprising a plurality of conformal filters and one or more associated LUTs. The conformal filters may comprise tunable filters, which are traditionally intended for single bandpass transmission, which are designed to enable tuning to a plurality of different configurations. Each configuration may be designed to filter interacted photons, generated by illuminating a sample, that conform to one or more spectral shapes associated with an analyte of interest. Interacted photons may comprise at least one of the following: photons absorbed by a sample, photons reflected by a sample, photons scattered by a sample, and photons emitted by a sample.

Conformal filter configurations may be determined by consulting the LUT that corresponds to the analyte. The LUT may comprise at least one voltage associated with each stage of the tunable filter. These voltages may be such that when applied to the associated stage, the tunable filter conforms to a spectral shape associated with the analyte. LUTs may be modified, providing the appropriate conformal filter configurations for detecting a variety of different analytes.

Examples of tunable filters that may be configured for use as a conformal filter may include: a liquid crystal tunable filter, an acousto optical tunable filter, a Lyot liquid crystal tunable filter, an Evans Split-Element liquid crystal tunable filter, a Solc liquid crystal tunable filter, a Ferroelectric liquid crystal tunable filter, a Fabry Perot liquid crystal tunable filter, and combinations thereof. In one embodiment, the tunable filter may comprise a MCF. A MCF is an imaging filter with serial stages along an optical signal path in a Solc filter configuration. Angularly distributed retarder elements of equal birefringence are stacked in each stage with a polarizer between stages. The retarders can include tunable (such as abutted liquid crystals tuned in unison), fixed and/or combined tunable and fixed birefringences. In one embodiment, quartz retarders may be used. Although the retardations are equal within each stage, distinctly different retardations may be used for two or more different stages. This causes some stages to pass narrow bandpass peaks and other stages to have widely spaced bandpass peaks. The transmission functions of the serial stages are superimposed with selected tunable peaks coinciding. The resulting conjugate filter has a high finesse ratio and good out of band rejection.

In one embodiment, the MCF may comprise filter technology available from ChemImage Corporation of Pittsburgh, Pa. This technology is further described in the following U.S. patents and published U.S. patent applications, which are hereby incorporated by reference in their entireties: U.S. Pat. No. 6,992,809, entitled "Multi-Conjugate Liquid Crystal Tunable Filter," U.S. Pat. No. 7,362,489, also entitled "Multi-Conjugate Liquid Crystal Tunable Filter," No. 2012/0300143, entitled "VIS-NIR Multi-Conjugate Liquid Crystal Tunable Filter," and No. 2011/0279744, entitled "Short Wave Infrared Multi-Conjugate Liquid Crystal Tunable Filter."

FIGS. 1A-1E illustrate conformal filter embodiments comprising a MCF 100a which may operate in conjunction with one or more LUTs (not illustrated). In FIG. 1A, a hot mirror 135 may be operatively coupled to the MCF 100a. A plurality of filter stages 115, 120, 125, and 130 may be arranged in a Solc configuration. Each stage may comprise a combination of polarizers 145a-145e, liquid crystal (LC) cells 150a-150d, and quartz retarders 155a-155b. A first antireflective (AR) glass component 140a may be placed in front of the first polarizer 145a and a second AR glass component 140b may be placed after the last polarizer 145e. The filter may be operatively coupled to a temperature sensor 170 for monitoring the temperature of the filter and modifying the LUT as needed for temperature adjustments. Predicted transmission of the filter operating in both a bandpass and a conformal mode is also provided 105a.

Figure 1B:
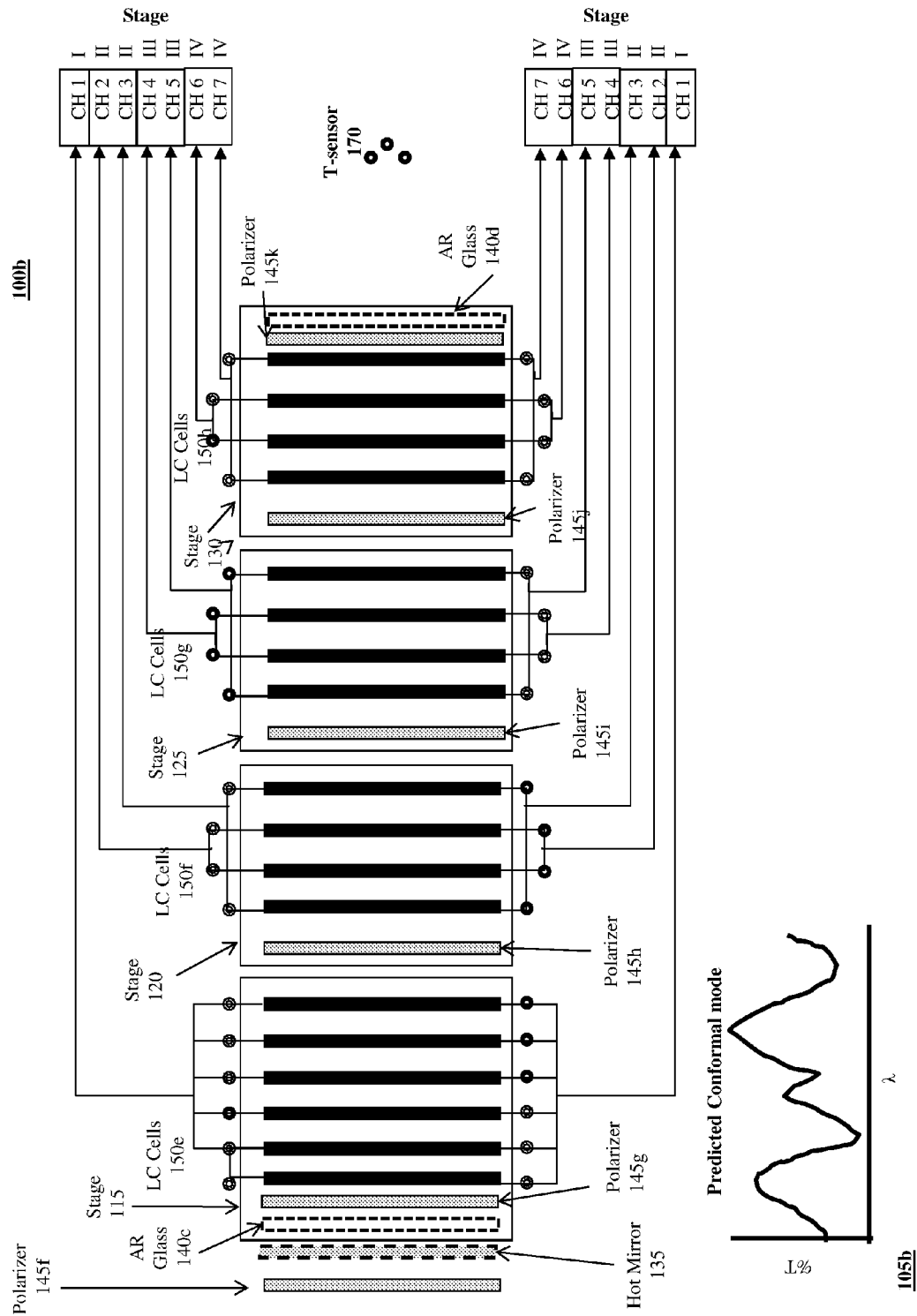
Figure 1C:
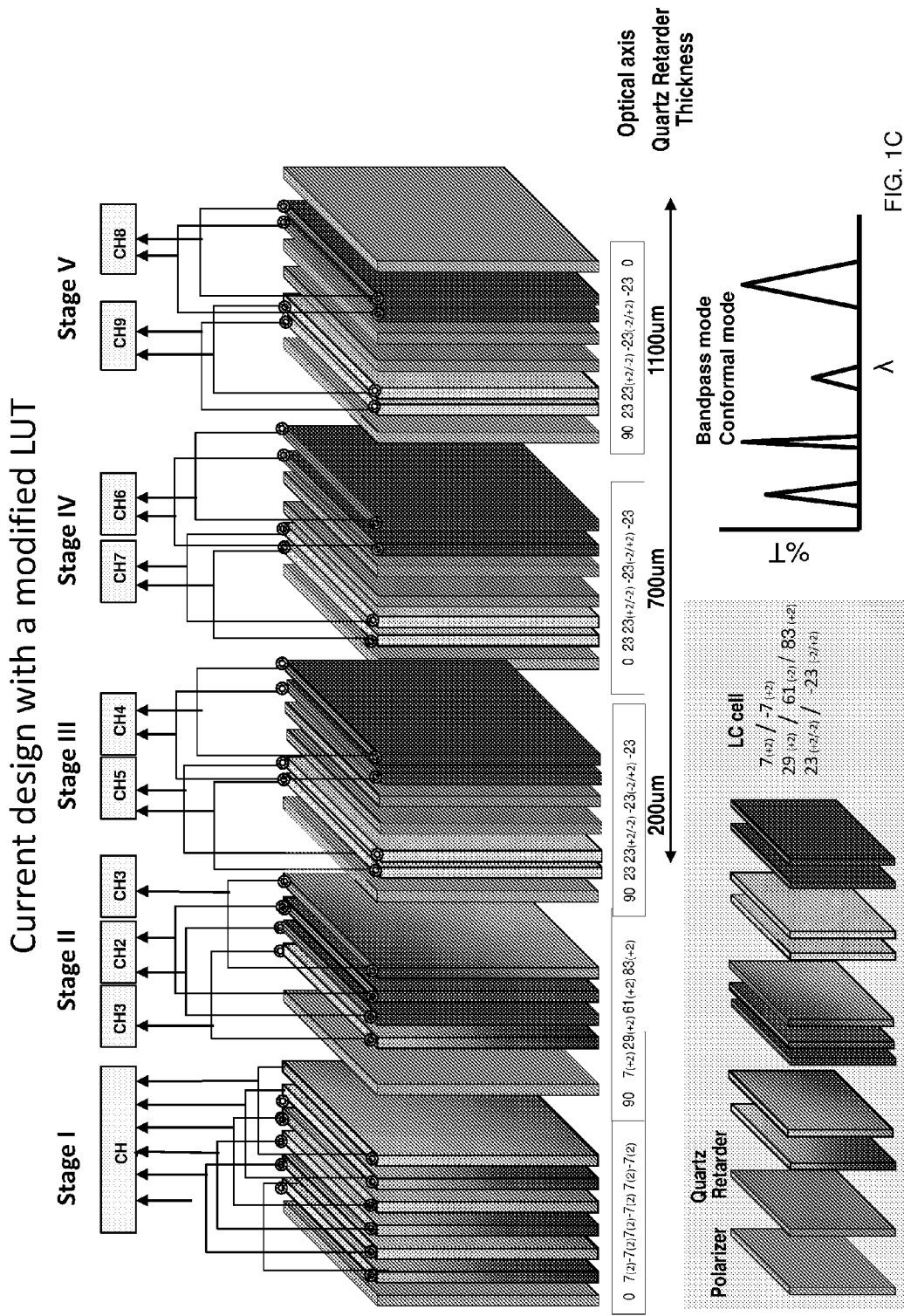
Figure 1D:
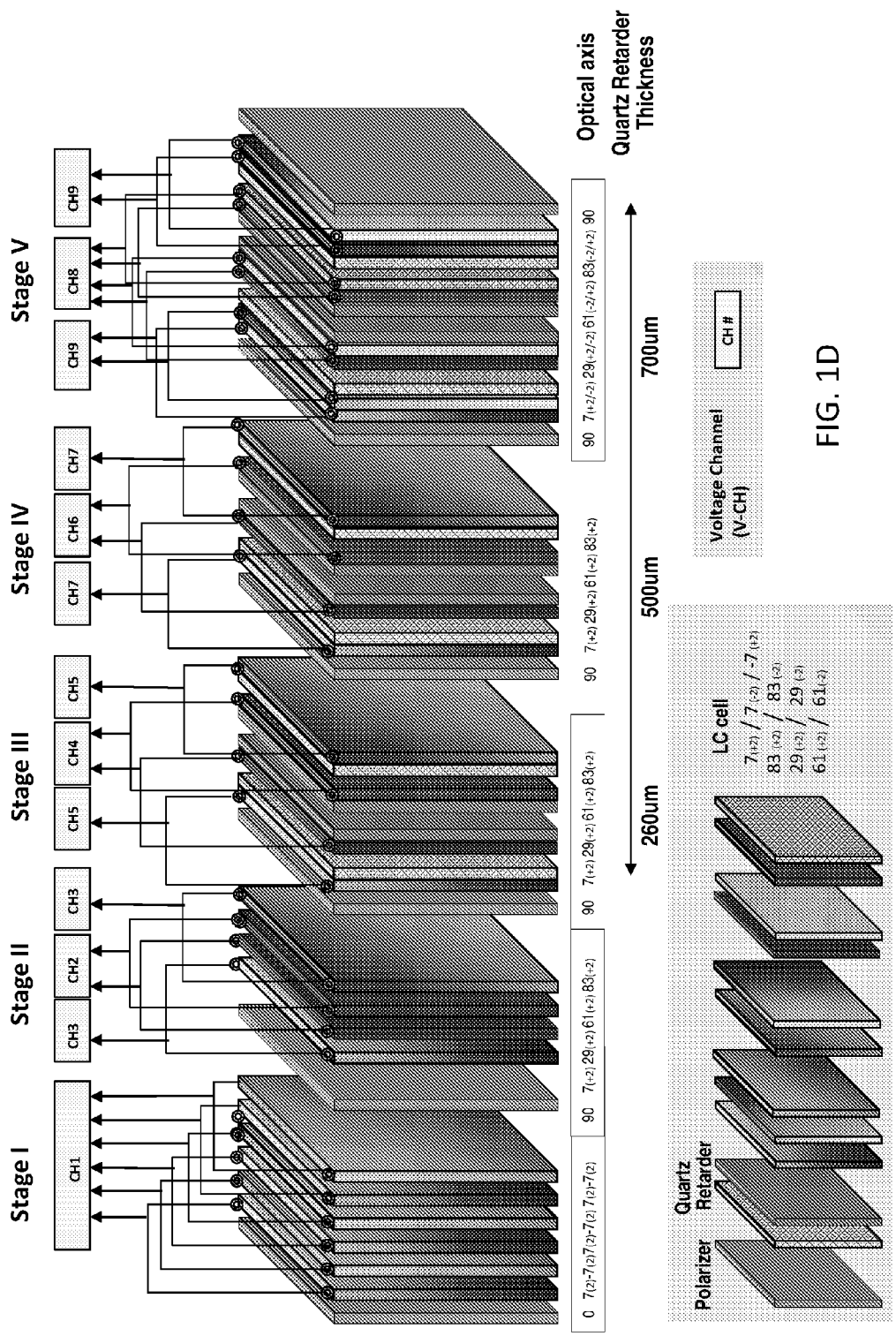

In FIG. 1B, the MCF 100b may comprise a polarizer 145f operatively coupled to the hot mirror 135 at an input of the MCF. The polarizer 145f may be mounted to a rotatable aperture for increasing optical throughput. In one embodiment, the polarizer 145f may be at least one of the following: a mechanically rotatable polarizer and an electronically tunable LC cell. The polarizer 145f may be tuned as needed each time the MCF 100b is tuned to a new configuration. Filter stages 115, 120, 125, and 130 may further comprise a combination of polarizers 145g-145k and liquid crystal (LC) cells 150e-150h. A first antireflective (AR) glass component 140c may be placed in front of polarizer 145g, and a second AR glass component 140d may be placed after the last polarizer 145k. Predicted transmission of the MCF operating in conformal mode is also provided 105b. FIG. 1C is illustrative of another MCF configuration that may be used with a modified LUT to achieve the objectives of the present disclosure. FIG. 1D is illustrative of still another MCF configuration that may be used with a modified LUT to achieve the objectives of the present disclosure.

Figure 1E:
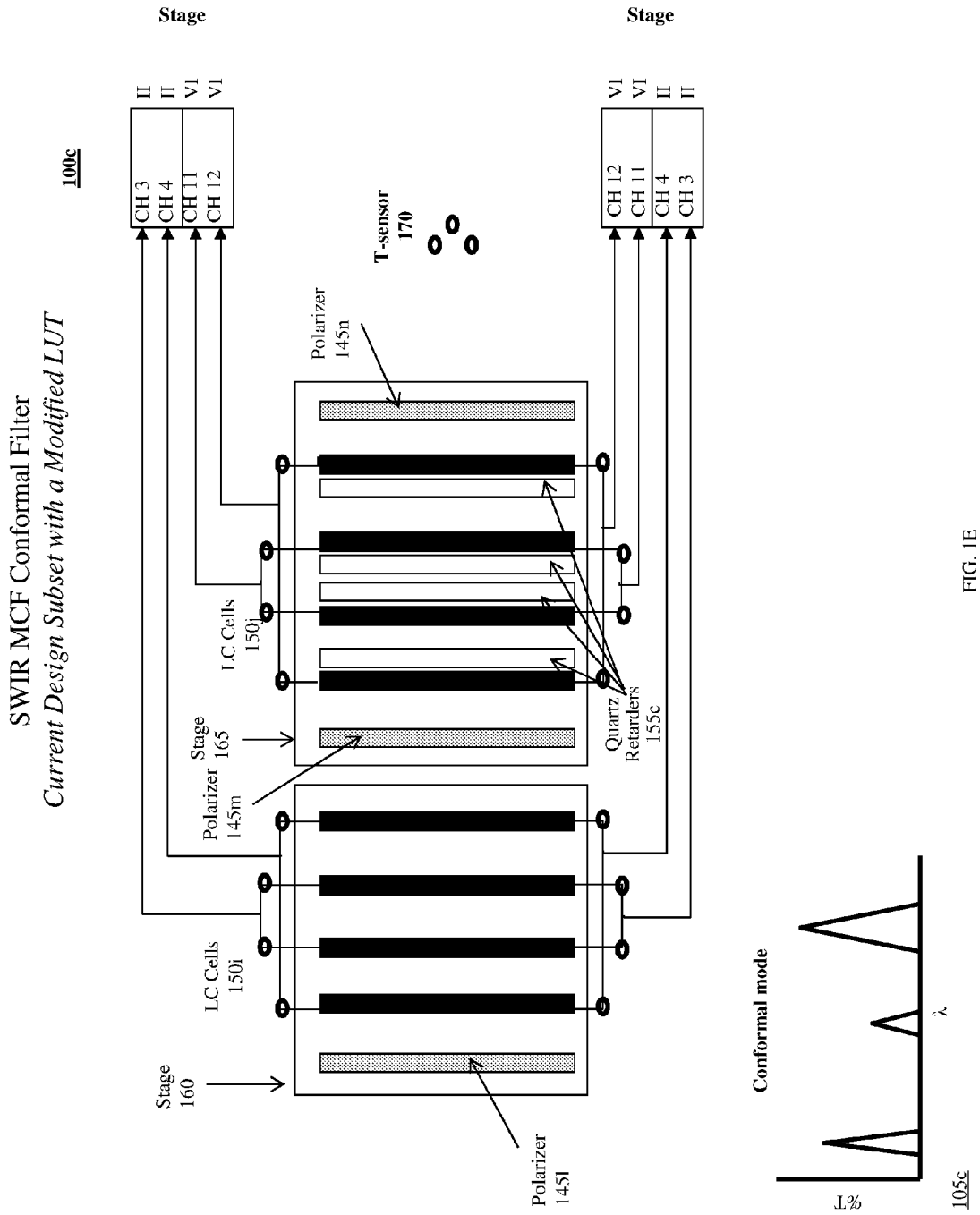

In another embodiment, the present disclosure provides for a plurality of conformal filters which comprise modified MCFs. In such an embodiment, tunable filters may be modified or specifically designed so that selected individual stages of a traditional tunable filter comprise multiple lower-resolution liquid crystal cells. As illustrated by FIG. 1E, a MCF may be redesigned with fewer stages 160 and 165 for use as a conformal filter 100c. Selected filter stages 160 and 165 may comprise a combination of optical elements including polarizers 145l-145n, LC cells 150i-150j, and quartz retarders 155c. Predicted transmission of the conformal filter is also provided 105c. The present disclosure contemplates that other configurations may be used to modify the MCF and that is not limited to the designs presented herein. Other conformal filter designs may be selected using a robust, iterative, non-linear optimization methodology. Such a methodology may begin with a random starting configuration and be reconfigured until a minimum response is achieved. The present disclosure contemplates that any iterative, non-linear optimization method known in the art may be applied to design the conformal filter.

In one embodiment, the conformal filters may be tuned to filter interacted photons that conform to one or more of the same spectral shapes. In another embodiment, the conformal filters may be tuned to filter interacted photons that conform to different spectral shapes. In such an embodiment, a system comprising this configuration may hold potential for simultaneous analysis of a plurality of analytes of interest. The present disclosure contemplates that a plurality of conformal filters may be incorporated into any detection system utilizing dual polarization. Exemplary embodiments of dual polarization configurations are illustrated in FIG. 2 and FIG. 3.

Figure 2:
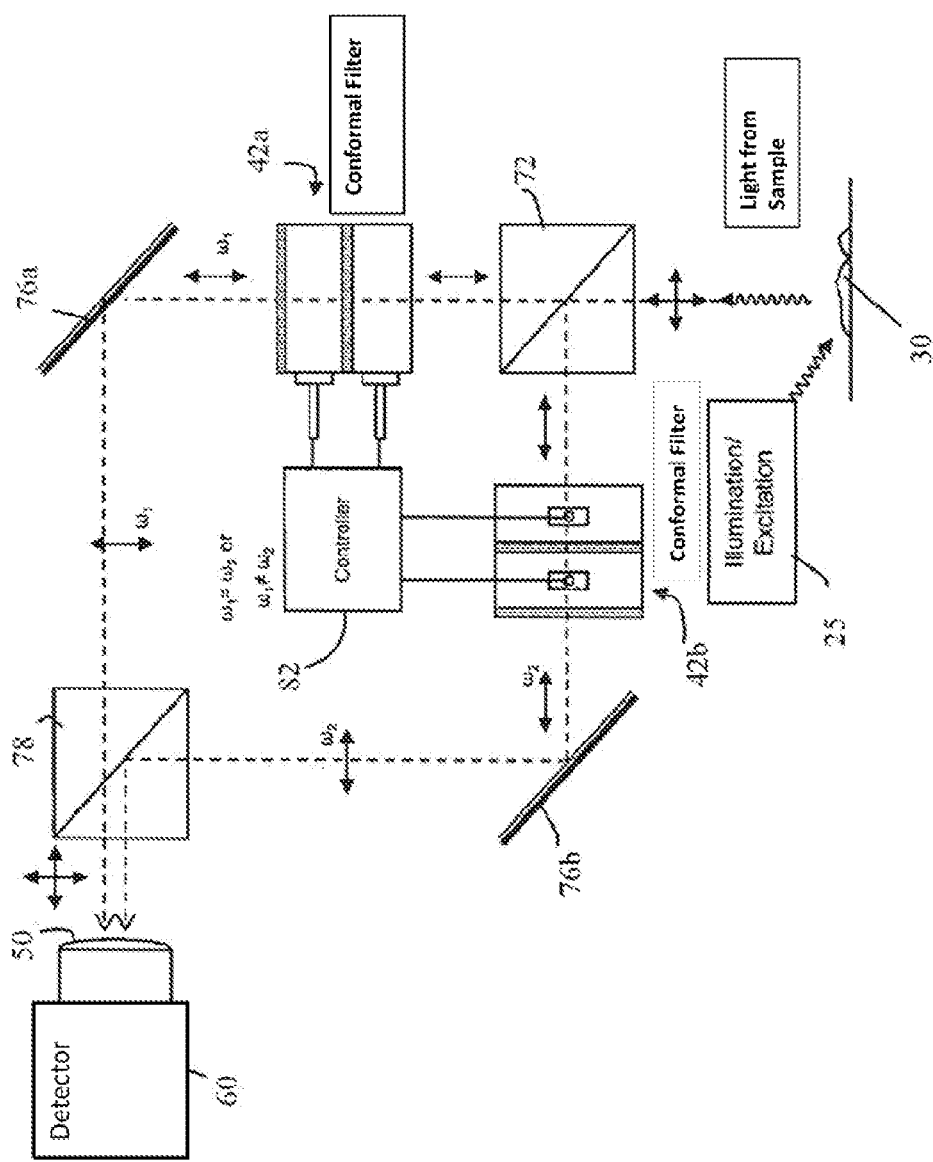
FIG. 2 is a schematic representation of a dual polarization configuration of the present disclosure.
Figure 3:
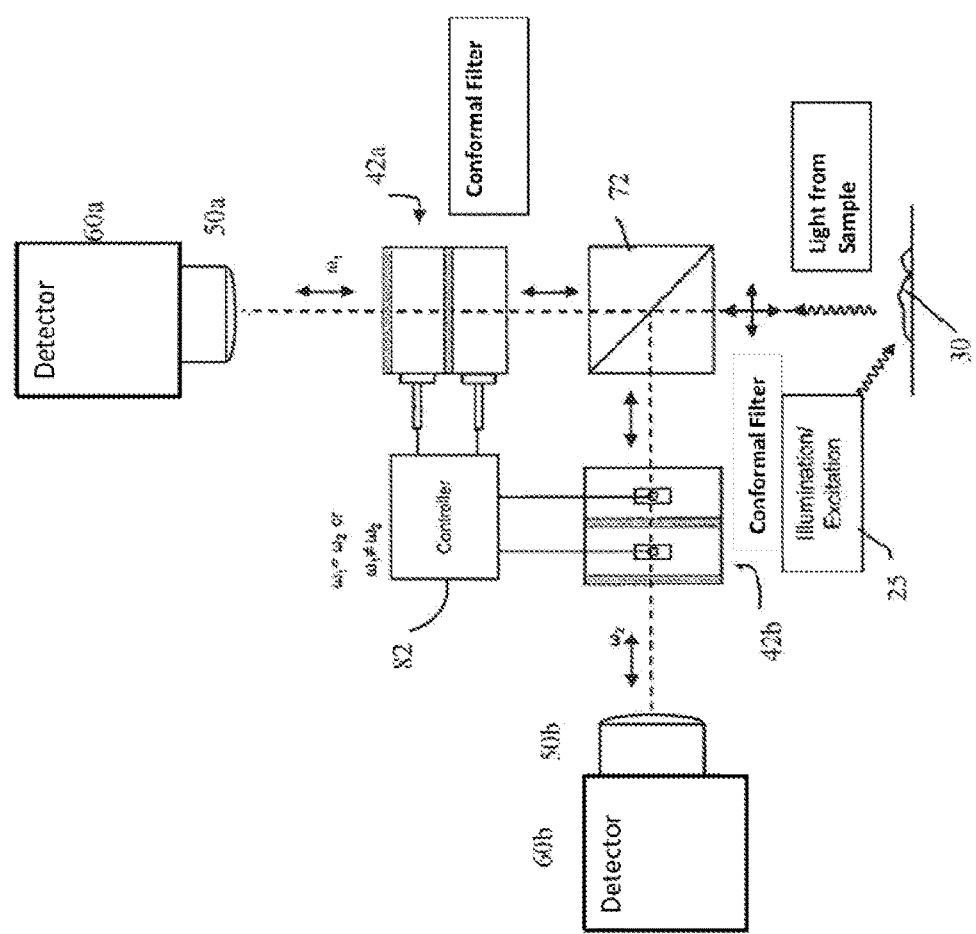
FIG. 3 is a schematic representation of a dual polarization configuration of the present disclosure.

Referring now to FIG. 2, the sample 30 may be illuminated and/or excited by an illumination source 25. In one embodiment, the illumination source 25 may comprise a laser. In another embodiment, the illumination source may comprise a passive illumination source such as solar radiation. In one embodiment, a laser may illuminate the sample directly in an oblique direction.

The embodiment of FIG. 2 comprises two independently tunable conformal filters 42a, 42b along distinct orthogonal beam paths for the orthogonal components emerging from polarizing beamsplitter 72. In one embodiment, the conformal filters may comprise at least one of: a multi-conjugate liquid crystal tunable filter, an acousto-optical tunable filter, a Lyot liquid crystal tunable filter, an Evans split-element liquid crystal tunable filter, a Solc liquid crystal tunable filter, a ferroelectric liquid crystal tunable filter, a Fabry Perot liquid crystal tunable filter, and combinations thereof. The conformal filters may comprise at least one of a modified liquid crystal tunable filter and a liquid crystal tunable filter configured to operate in conjunction with a LUT.

In this arrangement, the paths of the filtered beams are not parallel through the conformal filters 42a, 42b, but are directed by appropriate reflectors (e.g., mirrors) 76a, 76b to a beam combiner 78 (which may be a polarizing cube or polarizing beam splitter as illustrated) at which the orthogonal components, which can be at the same or different spectral shapes, are combined. In one embodiment, the components may be combined and directed to a detector 60 through a lens assembly 50. In another embodiment, the components may be kept separate as they are directed to the detector 60. However, the beam paths from one beam splitter 72 to the other 78 (via individual LCTFs 42a, 42b) may be made symmetrical to avoid, for example, the need for infinitely-corrected optics.

In FIG. 2, the detector 60 comprises a CCD detector. However, the present disclosure contemplates that the detector 60 may comprise other types of detectors including but not limited to: a CCD detector, a CMOS detector, an InGaAs detector, a platinum silicide (PtSi) detector, indium antimonide (InSb) detector, a mercury cadmium telluride (HgCdTe) detector, a colloidal quantum dot (CQD) detector, and combinations thereof. In some embodiments each or the combination of the above-listed detectors is a FPA detector. In some embodiments, each of the above detectors may include quantum dots to tune their bandgaps and/or alter sensitivity to different wavelengths.

In FIG. 2, the two conformal filters 42a, 42b may be tuned in unison using a conformal filter controller 82. It is possible to configure the controller 82 to independently tune the conformal filters 42a, 42b that respectively process orthogonal components of the input. Therefore, by appropriate control, the conformal filters can be tuned to the same spectral shape or to two different spectral shapes at the same time. The controller 82 may be programmable or implemented in software to allow a user to selectively tune each conformal filter 42a, 42b as desired.

In the embodiment of FIG. 2, a fast switching mechanism (not shown) may be provided to switch between the two views (or spectral images) corresponding to spectral data collected by the detector 60 from each of the conformal filters 42a, 42b. Alternatively, the two spectral views or images (from two separate conformal filters) may be combined or overlaid into a single image, for example, to increase contrast or intensity or for comparison purposes. The embodiment in FIG. 2 is shown to include a single CCD detector 60 to capture the filtered signals received from the conformal filters 42a, 42b.

In another embodiment, the reflectors 76a, 76b, and the beam combiner 78 may be removed, and two detectors may be used. An exemplary embodiment of such a configuration is illustrated in FIG. 3. Each detector 60a and 60b may be optically coupled to a corresponding one of the two conformal filters 42a, 42b to capture filtered signals from the conformal filters and to responsively generate electronic signals that enable display of spectral images of the illuminated sample 30. The present disclosure contemplates that any number of optical filters and associated detectors may be used to achieve the benefit of dual polarization as described herein.

In one embodiment, the two filtered signals may be detected simultaneously. As discussed herein, simultaneous detection of two different wavelengths holds potential for real-time detection when displayed in a non-overlapping configuration (side-by-side, top to bottom, etc.). In another embodiment, the two filtered signals may be detected sequentially.

It is noted here that although laser light may be coherent, the light received from the sample 30 (e.g., light emitted, scattered, absorbed, and/or reflected) and fed to the conformal filters 42a, 42b may not be coherent. Therefore, wavefront errors may not be present or may be substantially avoided in the two conformal filter versions in FIGS. 2 and 3 because of processing of non-coherent light by each conformal filter 42a, 42b.

The present disclosure also provides for a method for selecting a conformal filter configuration using an iterative process. This method is referred to herein as Real-time Contrast Enhancement (RtCE) and provides for configurations with high analyte specificity and sensitivity by applying active tunable filter voltage adjustment and feedback from a live measurement scene. Such an approach may be used to calibrate a conformal design for an analyte of interest, refine a previous conformal filter design for an analyte of interest, and/or generate a new conformal filter design for an analyte of interest.

Figure 4:
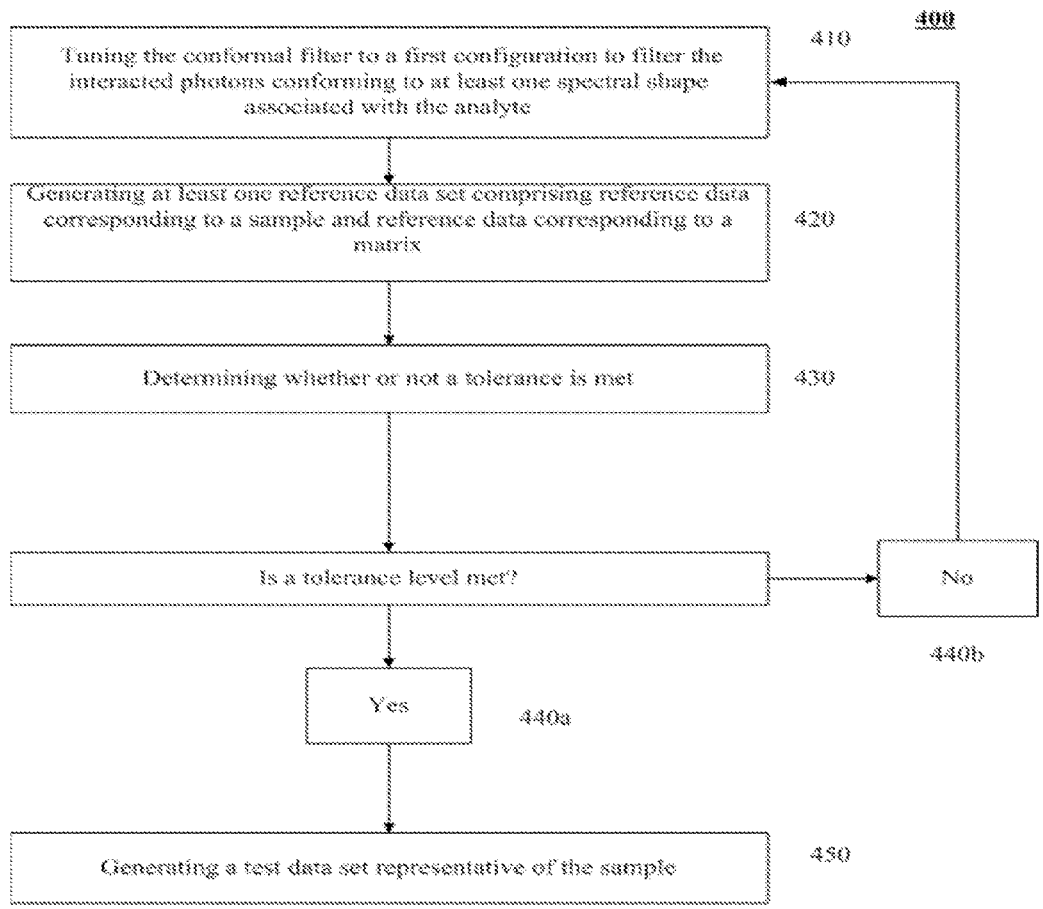
FIG. 4 is representative of a method of the present disclosure.

One embodiment of this optimization process is provided in FIG. 4. The method 400 may comprise tuning a conformal filter to a first configuration to filter interacted photons conforming to at least one spectral shape associated with an analyte in step 410. In step 420, at least one reference data set may be generated comprising reference data corresponding to a sample and reference data corresponding to a matrix. In one embodiment, the reference data set may comprise at least one reference spectrum associated with the sample and at least one reference spectrum associated with the matrix.

In another embodiment, the at least one reference data set may comprise at least one reference image comprising the sample and the matrix. A first region of interest may be selected corresponding to the sample, and a second region of interest may be selected corresponding to the matrix. Spectral data may be extracted from these regions of interest.

In one embodiment, at least one chemometric technique may be applied to the at least one reference data set (e.g. spectral data). Examples of chemometric techniques include, but are not limited to: correlation analysis, principle component analysis, principle component regression, partial least squares, multivariate curve resolution, Mahalanobis distance, Euclidian distance, band target entropy, band target energy minimization, partial least squares discriminant analysis, adaptive subspace detection, and combinations thereof. Chemometric techniques may be used to compare test data to reference data.

One or more optical computations may also be applied to the test data set. In one embodiment, this optical computation may comprise at least one of the following: T1, T1-T2, and (T1−12)/(T1+T2). Other optical computations known in the art may also be applied and the present disclosure should not be construed as to be limited to those specified herein.

A determination of whether or not a tolerance level is met may be made in step 430. In one embodiment, this determination may comprise applying at least one Figure of Merit (FOM). A FOM is a numerical value that may be used to guide the optimization process. Examples of FOM that may be applied include, but are not limited to: standard error of calibration (SEC), Euclidian distance, standard error of prediction (SEP), 1-area under the receiver operator characteristic curve (AUROC), optical throughput (% T), and combinations thereof. Other FOMs may be used that incorporate optical throughput, signal to noise ratio (SNR), and the like. If a tolerance level is met 440a, then a test data set representative of the sample may be generated in step 450. If a tolerance level is not met 440b, then the process may be repeated for at least one other conformal filter configuration until a tolerance level is met.

In another embodiment, the present disclosure provides for a system comprising a processor and a non-transitory processor-readable storage medium in operable communication with the processor. The storage medium may contain one or more programming instructions that, when executed, cause the processor to tune the conformal filter to a first configuration and filter interacted photons conforming to at least one spectral shape associated with an analyte of interest, generate at least one test data set representative of the sample, and analyze the test data set to assess the sample for at least one characteristic of the analyte. The storage medium may further contain programming instructions that cause the processor to select conformal filter configurations by searching a LUT corresponding to an analyte and applying the configuration to the conformal filter.

In another embodiment, the system may further comprise one or more programming instructions that, when executed, cause the processor to iteratively configure the conformal filter until a tolerance level is met. In such an embodiment, the instructions may cause the processor to tune the conformal filter to a first configuration to filter interacted photons conforming to at least one spectral shape associated with the analyte, generate at least one reference data set comprising reference data corresponding to the sample and reference data corresponding to a matrix, and determine whether or not a tolerance level is met. If a tolerance level is met, a test data set may be generated. If a tolerance level is not met, then the steps may be repeated for one or more difference configurations until a tolerance level is met. In one embodiment, whether or not a tolerance level is met may be determined by the processor applying at least one figure of merit. In other embodiments the processor may further analyze the test data set by applying at least one of the following: an optical computation and a chemometric technique.

The present disclosure contemplates that the conformal vision system and method disclosed herein may be applied in a wide variety of applications. In one embodiment, conformal vision may be used to detect pests and/or insects. The conformal vision device can detect and differentiate waste residues/droppings of different pests (mice, rats, bats, cockroaches, bed bugs, wasps/yellow jackets/bees, termites, ants etc.)

In another embodiment, conformal vision can be used to detect the level of stress in a person. In such a "distress detection" configuration, conformal vision can be used to assess the level of oxygenation of tissue, and correlate this to a stress level. Such a detector can be applied to interrogation situations (is a detainee telling the truth?), or in building/transportation security (is there a passenger that is more distressed than average?).

Conformal vision can also be applied in dermatological applications, such as analyzing the skin for the presence of rashes or other irritants, identifying the source of the rash, assessing the effectiveness/usefulness of a treatment (for example, lotion for poison ivy), and detecting various skin allergies. In some embodiments, conformal vision may be applied to analyze skin for the presence of wrinkles, age spots, and other facial flaws.

In another embodiment, conformal vision can be applied to detect the freshness of food. For example, conformal vision could be applied by the food industry to assess ripeness in produce, to assess purity of a food (sugar, flour, etc.), and to enable automated defect rejection by machinery. The food industry could also apply conformal vision to assess freshness of food, such as bread and cheese, and to detect mold and other indicators of staleness. Similarly conformal vision can be applied to the analysis of alcohol. For example, in the analysis of wine, an assessment may include measuring variants in wine, the maturity of grapes and/or wine in process, or the ability to distinguish types of wine.

Conformal vision can also be applied in crime scene investigation and forensic applications, such as by detecting dried blood. The system and method can also be applied to analyze objects and/or materials to determine whether or not they are counterfeit. For example, money, jewelry, pure chemical materials in a factory or store, art work, and/or objects can be analyzed.

In another embodiment, conformal vision can be applied in a number of different color matching applications. Color matching can be applied in home improvement (paint, carpet, furniture, etc.) and cosmetic (makeup, hair color, etc.) applications.

In another embodiment, conformal vision may be applied to Human Self-Assessment. For example, the technology can be operably coupled to a television, mirror, camera, projector or other device for projecting an image. An assessment can be made regarding clothing, physical appearance and the like. In further embodiments and modifications, the human self-assessment may be displayed as an image on the above television, mirror, camera, projector, or other device for projecting an image may be paired with a virtual reality device or software interface.

When the embodied conformal vision system is applied to Human Self-Assessment, the system for conformal vision may be incorporated into a variety of professional and consumer settings. For example, in a professional setting, the system for conformal vision is incorporated into medical devices that are present in a physician's office, a hospital, a clinic, a retail pharmacy, or other similar healthcare settings. In such professional settings, the conformal vision may be used as part of routine tests during a person's recurring visits to such a healthcare setting, though this is but one example of the invention and it is not intended to be limiting. A conformal vision system may also be used to assess useful patient information related to skin condition, heart health, respiration, skin differential blood flow, skin color, edema levels, and the like. Combinations of these features may also be assessed.

A conformal vision system may be used in other professional settings, such as beauty salons, hair care salons, spas, nail salons, skin treatment centers, gyms, health clubs, and the like. In such locations, the conformal vision system may be used to assess a person or customer's skin condition, heart health, respiration, hair condition, nail condition, clothing, mood, physical appearance, stress level, nervousness, physical fitness, tissue condition, and the like. Combinations of these features may also be assessed.

A conformal vision system may be used in a consumer setting, such as in a person's home, office, or vehicle. In such consumer settings, the conformal vision system may be used to assess a person's skin condition, heart health, respiration, hair condition, nail condition, clothing, mood, physical appearance, stress level, nervousness, physical fitness, tissue condition, and the like. Combinations of these features may also be assessed.

In some professional and consumer settings, a conformal vision system is used to assess analytes that are relevant to the location that the person occupies. For example, the conformal vision system may be used in an vehicle such as an automobile, motorcycle, boat, or airplane to detect whether a person has consumed alcohol or intoxicating drugs and trigger a warning or prevent the vehicle from operating if it detects pre-specified levels of the alcohol or intoxicating drugs. In other embodiments, the conformal vision system may be used in a person's home to assess mood or other condition so that the person may determine whether their selected wardrobe matches the mood. In still further embodiments, the conformal vision system may be used to analyze the effectiveness of a skin, hair, or beauty treatment that was applied in a beauty salon, hair care salon, nail salon, or the like.

In the above professional and consumer settings, the system for conformal vision may be configured to detect analytes of interest depending on the need and setting. The analytes may be or may be indicative of tissue oxygenation, blood alcohol level, the presence of aromatic compounds such as those found in perfumes, the presence of contaminants, the presence of insects or insect residues or waste products, the presence of drugs, the presence of bacteria, urea, lactic acid, and the like. In further embodiments, the analytes may indicate the presence of one or more conditions including melanoma and other skin cancers, edema or swelling of the skin, diabetes (as indicated by oxygenation of skin tissue in extremities), blood sugar level, blood vessel conditions such as varicose veins, acne vulgaris, blood pressure, wound healing, psoriasis, and other conditions and indicators particular to the skin or dermis. In still further embodiments, the analytes may be measured in the eye, and include compounds of and indicators of blood cholesterol, blood plaque, blood pressure, tissue oxygenation, and the like, as well as any of the above indicators and conditions. Each of the above compounds or indicators may be used to determine a wellness factor that is generated by the system for conformal vision.

FIGS. 6A-6E illustrates exemplary housing configurations for incorporating a conformal vision device into a cell phone or other mobile communication device. In FIGS. 6A-6E, a system for conformal vision 201 can perform a self-assessment or can be used to determine the presence of analytes. The system 201 includes at least a device 203 having components such as the conformal filter, detector, processor, and look-up table (see cutaway, individual components not shown). The conformal filter may include a tunable filter. The system 201 also includes a cell phone or other mobile communication device 205, though other electronic devices are also contemplated.

It is contemplated that the embodiments show in FIGS. 6A-6E can have a variety of configurations for the different components of the system 201 depending on requirements for performance, device size and packaging, power consumption, and so forth. For example, if the analyte of interest is compatible with analysis under VIS wavelengths, the system 201 may be configured so that the detector is the CMOS or CCD sensor for the camera that is already integrated into the cell phone or other mobile communications device. In another embodiment, the CMOS or CCD sensor for the camera in the cell phone or other mobile communications device may be combined with an external sensor that is provided in a module (not separately shown) of the system 201, enabling sensitivity for both VIS wavelengths and another spectra of interest. The other spectra of interest depends on the analytes that are to be detected and may include UV, NIR, SWIR, Milt, LWIR, and overlapping ranges.

In some embodiments, the module is detachable from the cell phone or mobile communications device. In some embodiments, the module includes additional features to improve functionality of the system 201, such as an auxiliary battery or other power source to compensate for additional power consumption required by the system 201.

FIG. 7 illustrates an exemplary mode of operation of a conformal vision device of the present disclosure. In FIG. 7, the system for conformal vision is embodied in a cell phone or portable communications device and is being used to detect the residue or waste products of insects such as bedbugs. A user can quickly and accurately scan an area of interest to determine whether it has been infested with the insects. Such functionality is a significant improvement over prior art techniques for detecting insect infestation, which often require time-consuming search and examination of the area of interest and that the person searching has a significant degree of expertise and knows where to search and what indicators of infestation to search for.

Figure 8:
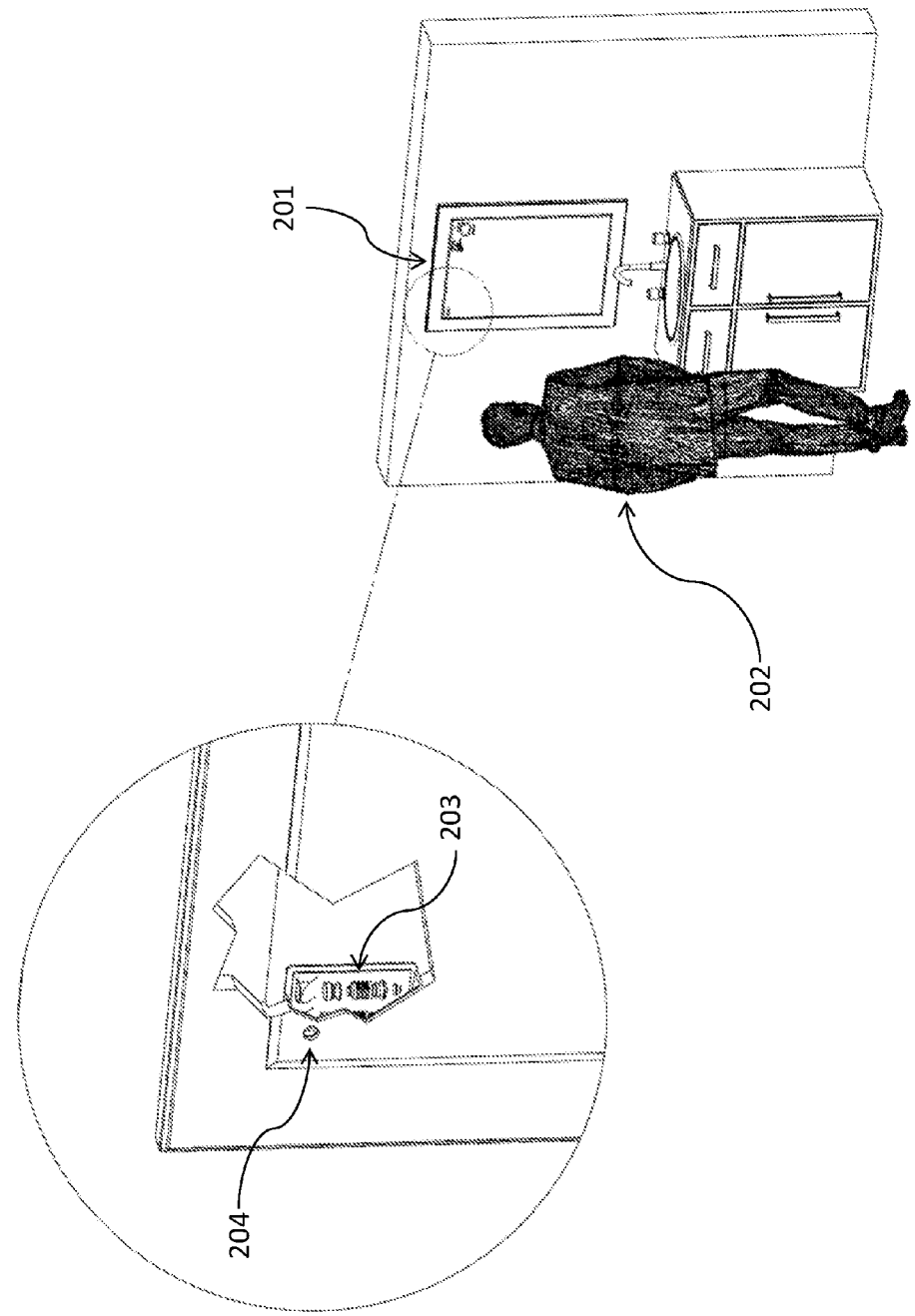
FIG. 8 is an exemplary application of the conformal filter.

FIG. 8 is illustrative of yet another embodiment of the invention. In FIG. 8, a user 202 can operate a system for conformal vision 201 to perform a self-assessment. The system for conformal vision 201 includes at least a device 203 that includes components such as the conformal filter, detector, processor, and look-up table (see cutaway, individual components not shown). The conformal filter may include a tunable filter. The system for conformal vision includes at least one aperture or transparent portion 204 that permits the wavelengths which are to be analyzed by the system for conformal vision 201 to pass through it.

While FIG. 8 displays the use and integration of the system for conformal vision 201 in a consumer or professional setting above a sink or in a lavatory, the invention is not so limited. The system for conformal vision 201 may be positioned in any location where its use would be beneficial, such as within a physician's office, a hospital, a clinic, a retail pharmacy, other similar healthcare settings, beauty salons, hair care salons, spas, nail salons, skin treatment centers, gyms, health clubs, a home, an office, a vehicle, an automobile, a motorcycle, a boat, or an airplane.

In some embodiments, the system for conformal vision is configured to measure an analyst or analytes non-invasively. In other embodiments, the system may also utilize other data and/or metadata that is inputted manually or automatically by a user or by another computer system or another person. For example, such metadata may include information from an electronic scale, a smart watch, a smartphone, a personal health sensor, a laptop or desktop computer, portable communications device, or a combination of the above devices. The use of multiple data sources provides additional information and context to the data that is collected by the system of conformal vision, which improves the usefulness of the health assessments and other determinations that are performed by the system for conformal vision.

Examples

Figure 5A:
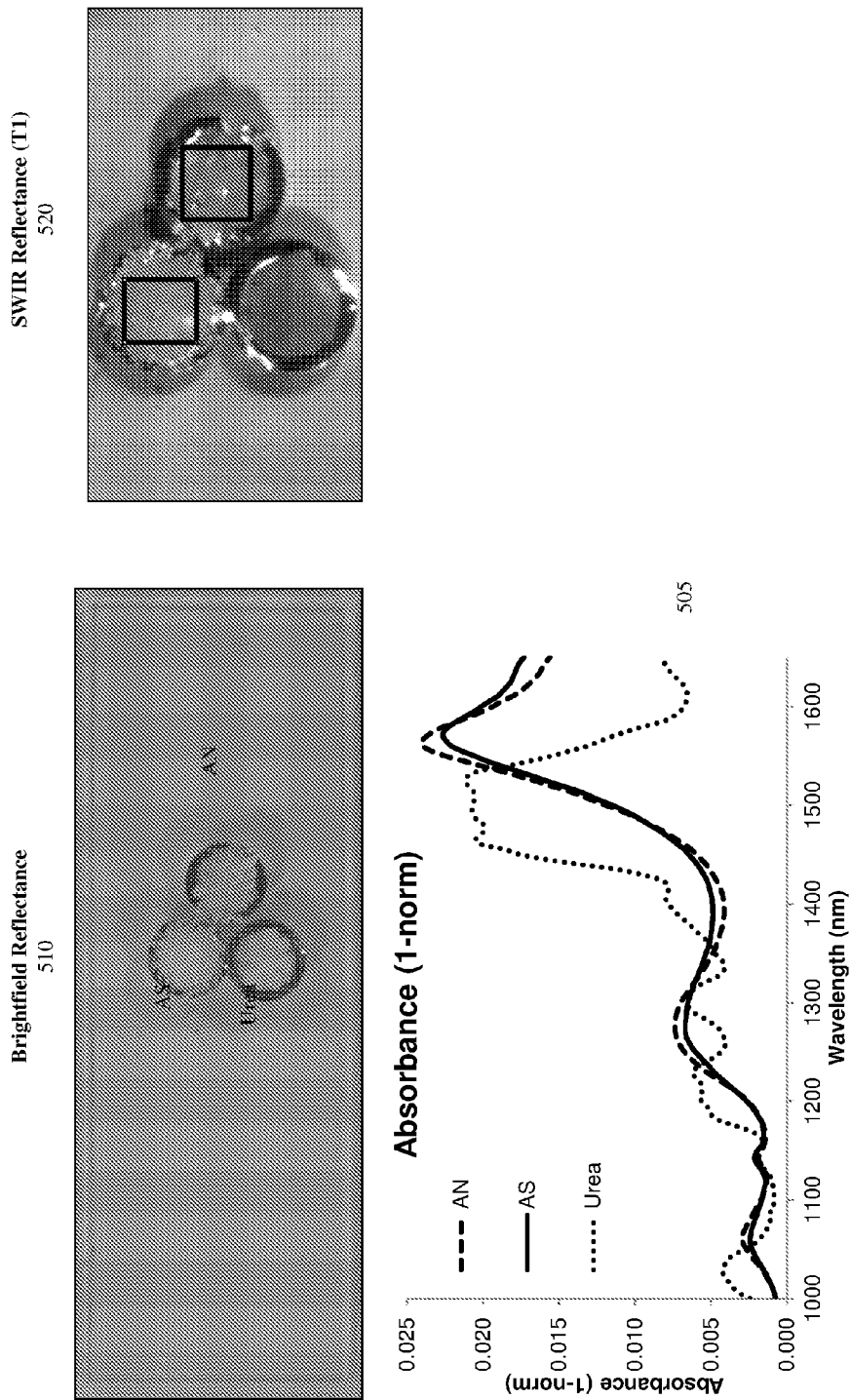
FIG. 5A is illustrative of the detection capabilities of the present disclosure.
Figure 5B:
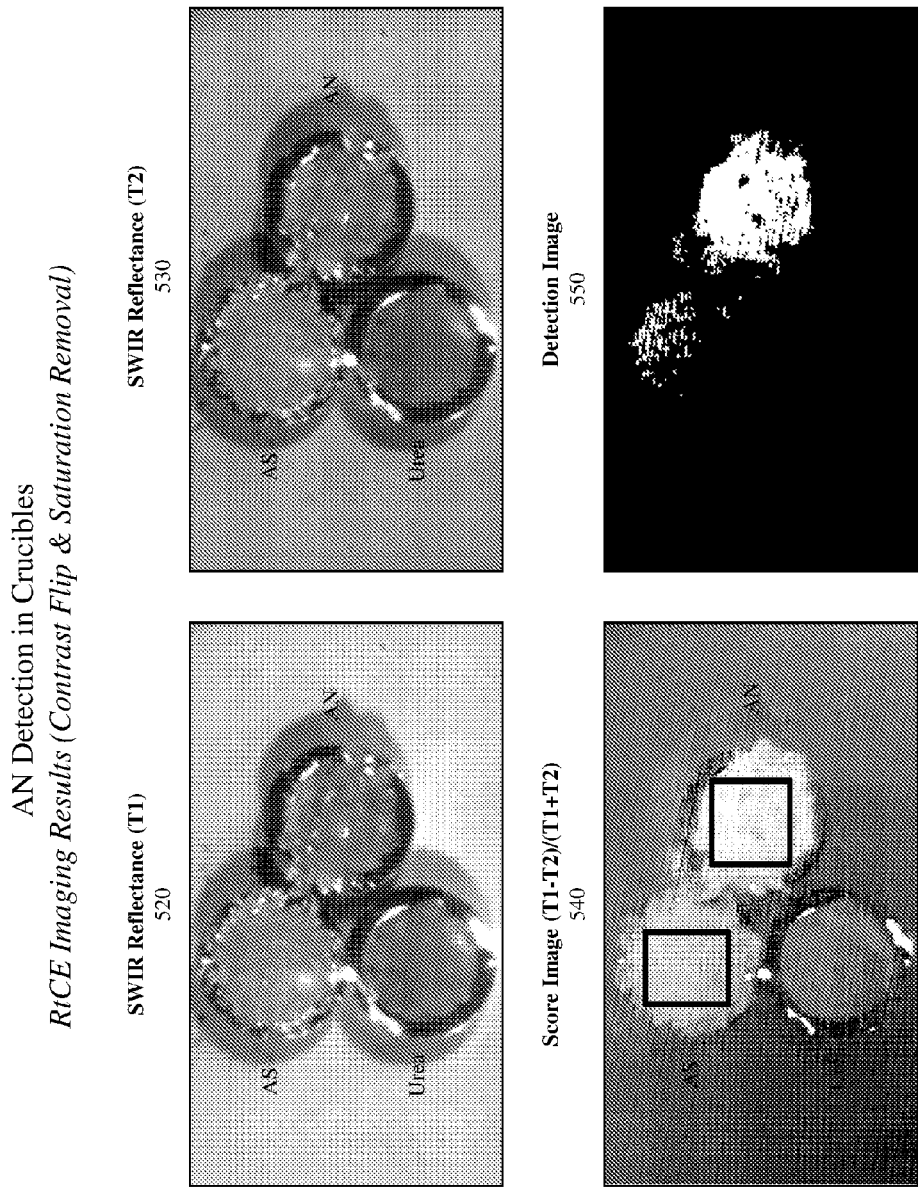
FIG. 5B is illustrative of the detection capabilities of the present disclosure.
Figure 5C:
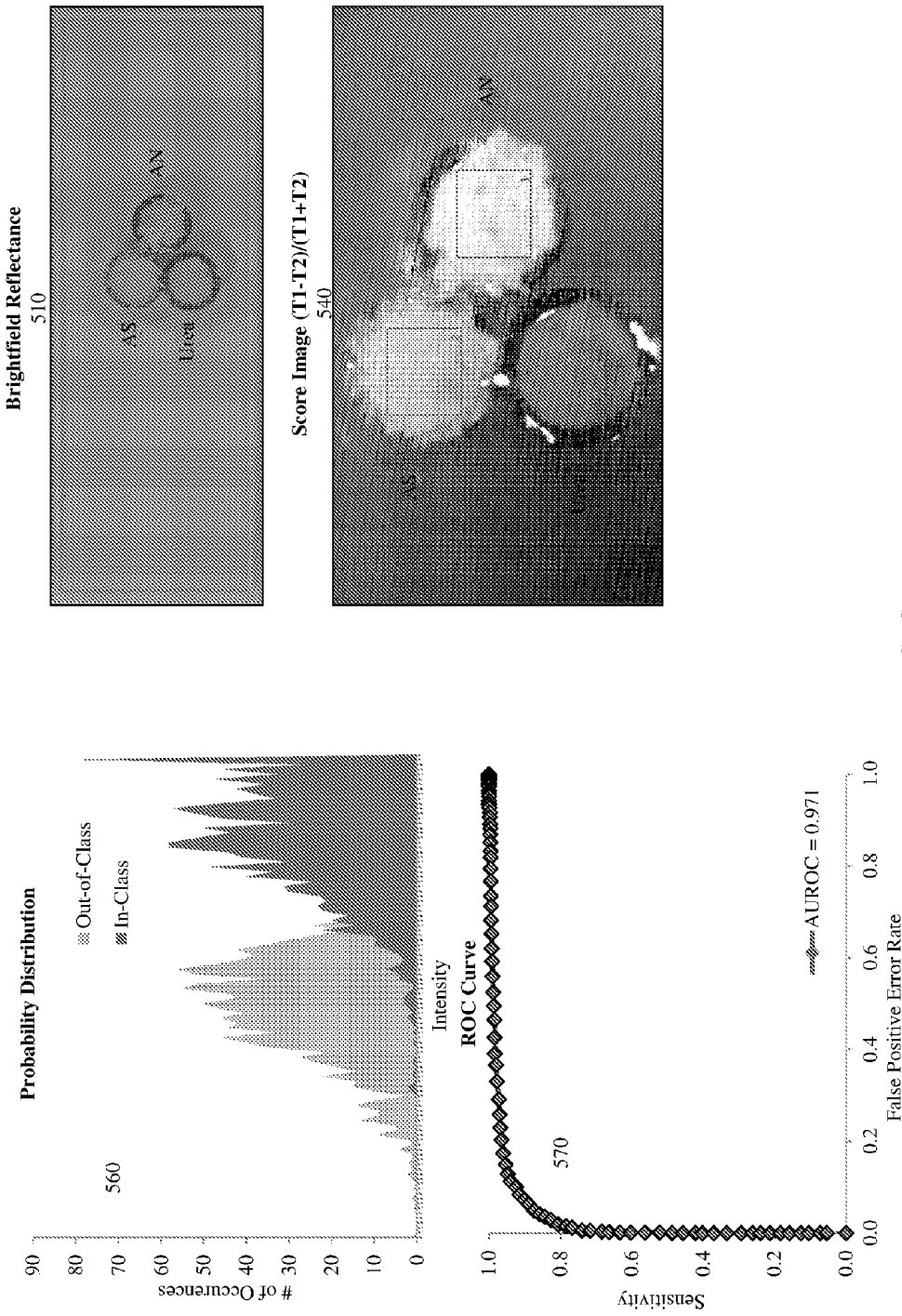
FIG. 5C is illustrative of the detection capabilities of the present disclosure.

FIGS. 5A-5C are illustrative of the detection capabilities of a conformal filter of the present disclosure. Conformal filter HSI differs from conventional HSI in that conformal filters rely on a robust design algorithm in order to produce an appropriate optical transmission function(s) for the intended analytical response as opposed to tuning to discrete wavelengths. As a result of the large spectral bandpass of the LC conformal filter, its optical throughput, and thus the measured SNR, is considerably higher than LC filters operated in a single wavelength mode. In addition, the conformal filter approach requires fewer measurements to achieve analyte specificity resulting in a faster measurement time as compared to conventional LC HSI. As shown in FIGS. 5A-5C, not only does the conformal approach provide better detection performance for the target analyte (highest AUROC over all methods), the detection is made faster and demonstrates excellent discrimination between "near neighbors," i.e., analytes with similar spectral features such as the Target Analyte and the Confusant in FIGS. 5A-5C.

Three samples were prepared comprising ammonium sulfate (AS), AN (ammonium nitrate), and urea ($CO(NH_2)_2$). AN was selected as the analyte of interest, AS was selected as a confusant (background), and urea was selected as an interferent. The samples were analyzed using an experimental set up in which the illumination source 215 comprised a quartz tungsten halogen lamp, the conformal filter 42 comprised a MCF, and the detector 60 comprised a SWIR camera. A brightfield reflectance image 510 and a SWIR reflectance image (T1) 520 were generated. Spectral data for each substance 505 is also illustrated in FIG. 5A.

FIG. 5B illustrates the detection capabilities of the present disclosure when an RtCE methodology is applied. A second SWIR reflectance image (T2) was generated 530. The optical computation (T1-T2)/(T1+T2) was applied, and a score image 540 was generated. As can be seen from the detection image 550, AN was easily detected and distinguished from AS and urea. FIG. 5C is illustrative of the detection results after applying additional processing steps such as contrast flip and saturation removal. A probability distribution 560, from the score image 540, illustrates in-class v. out-of-class detections. The ROC curve 570 illustrates the sensitivity and false positive results achieved. The ROC curve 570 was generated by applying a threshold to the probability distribution 560. As illustrated by the Examples, the system and method of the present disclosure hold potential for detecting analytes and discriminating between "near neighbors," i.e., analytes with similar spectral features.

While the disclosure has been described in detail in reference to specific embodiments thereof, it will be apparent to one skilled in the art that various changes and modifications can be made therein without departing from the spirit and scope of the embodiments. Additionally, while the examples provided herein related to specific analytes, the present disclosure is not limited to these analytes and may be used to detect a wide variety of analytes of interest. Thus, it is intended that the present disclosure cover the modifications and variations of this disclosure provided they come within the scope of the appended claims and their equivalents.

The invention claimed is:

1. A system for conformal vision, comprising:
a conformal filter that includes a tunable filter;
a detector that detects interacted photons through the conformal filter;
a processor in communication with the detector; and
a look-up table (LUT) associated with the conformal filter and which corresponds to an analyte of interest,
wherein at the conformal filter tunes to filter interacted photons conforming to a spectral shape associated with the analyte of interest,
wherein the processor generates a test data set representative of the sample from the detector,
wherein the processor analyzes the test data set to determine at least one characteristic of the analyte
wherein the system is configured for human self-assessment, and wherein the processor is operably coupled to at least one of a television, a mirror, a camera, or a device for projecting an image.

2. The system of claim 1, wherein the LUT comprises at least one voltage associated with each stage of each tunable filter.

3. The system of claim 1, wherein each tunable filter is selected from the group consisting of a liquid crystal tunable filter, an acousto tunable filter, a Lyot liquid crystal tunable filter, an Evans Split-Element liquid crystal tunable filter, a Sole liquid crystal tunable filter, a Ferroelectric liquid crystal tunable filter, a Fabry Perot liquid crystal tunable filter, a multi-conjugate filter (MCF) and combinations thereof.

4. The system of claim 1, further comprising a hot mirror.

5. The system of claim 1, wherein the detector is selected from the group consisting of a charged coupled device (CCD) detector, a complementary metal oxide semiconductor (CMOS) detector, an indium gallium arsenide (InGaAs) detector, a platinum silicide (PtSi) detector, a mercury cadmium telluride (HgCdTe) detector, a colloidal quantum dot (CQD) detector, and combinations thereof.

6. The system of claim 1, wherein the system is configured to assess a level of oxygenation in tissue.

7. The system of claim 1, wherein the system is configured to analyze skin for the presence of a rash or an irritant.

8. The system of claim 1, wherein the human self-assessment is with respect to clothing or physical appearance.

9. A method for conformal vision, comprising:
providing a look-up table (LUT) associated with a conformal filter and which corresponds to an analyte of interest, wherein the conformal filter includes a tunable filter,
tuning the conformal filters which includes the tunable filter, to filter interacted photons conforming to a spectral shape associated with an analyte of interest, generating, using a processor, a test data set representative of the sample from a detector,
analyzing, using the processor, the test data set to determine at least one characteristic of the analyte, and
displaying a human self-assessment image based on at least one characteristic of the analyte.

10. The method of claim 9, wherein the LUT comprises at least one voltage associated with each stage of the tunable filter.

11. The method of claim 9, wherein the at least one tunable filter is selected from the group consisting of a liquid crystal tunable filter, an acousto tunable filter, a Lyot liquid crystal tunable filter, an Evans Split-Element liquid crystal tunable filter, a Sole liquid crystal tunable filter, a Ferroelectric liquid crystal tunable filter, a Fabry Perot liquid crystal tunable filter, a multi-conjugate filter (MCF) and combinations thereof.

12. The method of claim 9, wherein the method further comprises:
generating a reference data set corresponding to a matrix;
applying a chemometric technique to the reference data set, and
outputting an enhanced contrast test data set that has enhanced contrast and that is representative of the sample so as to achieve Real-time Contrast Enhancement (RtCE).

13. The method of claim 12, wherein the method further comprises determining whether or not a tolerance level is met by applying at least one Figure of Merit (FOM).

14. The method of claim 13, wherein the FOM is selected from the group consisting of standard error of calibration (SEC), Euclidian Distance, standard error of prediction (SEP), 1-Area Under the Receiver Operator Characteristic Curve (ALTROC), optical throughput (% T), and combinations thereof.

15. The method of claim 12, wherein the chemometric technique is selected from the group consisting of correlation analysis, principle component regression, partial least squares, multivariate curve resolution, Mahalanobis distance, Euclidian distance, band target entropy, band target energy minimization, partial least squares discriminant analysis, adaptive subspace detection, and combinations thereof.

16. The method of claim 9, wherein the human self-assessment image includes information regarding the clothing or physical appearance of the human that is performing the self-assessment.

17. The method of claim 9, wherein displaying the human self-assessment image comprises displaying the human self-assessment image using a television, a mirror, a camera, or a projector.

18. A wellness indicating apparatus, comprising:
a conformal filter that includes a tunable filter, wherein the conformal filters tunes to filter interacted photons conforming to a spectral shape associated with an analyte of interest on a sample;
a detector; and
a processor, wherein the processor:
generates a test data set representative of the sample from the detector,
analyzes the test data set to determine at least one characteristic or the analyte,
correlates the at least one characteristic of the analyte to a determined wellness factor, and
communicates the determined wellness factor to a human user.

19. The wellness indicating apparatus of claim 18, further comprising a network interface for communicating the determined wellness factor to a human user.

20. The wellness indicating apparatus of claim 18, further comprising a display for communicating the determined wellness factor to a human user.

21. The wellness indicating apparatus of claim 20, wherein the display is selected from the group consisting of a liquid crystal display, an organic light emitting diode display, a projector, an electrophoretic display, a mirror, a cathode ray tube display, a projection display, a heads up display, an augmented reality display and combinations thereof.

22. The wellness indicating apparatus of claim 18, wherein the analyte is related to tissue oxygenation.

23. The wellness indicating apparatus of claim 18, wherein the wellness factor is related to a skin condition, a heart condition, a stress level, a mood, respiration, skin differential blood flow, skin color, edema levels, and combinations thereof.

24. A method of assessing wellness, comprising:
providing a conformal filter, wherein the conformal filter includes a tunable filter,
providing a detector,
providing a processor, wherein the processor is configured to:
generate a test data set representative of the sample from the detector,
analyze the test data set to determine at least one characteristic of the analyte,
correlate the at least one characteristic of the analyte to a determined wellness factor, and
communicate the determined wellness factor to a human user.

* * * * *